(12) United States Patent
Bhaskaran et al.

(10) Patent No.: US 7,465,823 B2
(45) Date of Patent: Dec. 16, 2008

(54) UTILIZATION OF ACETIC ACID REACTION HEAT IN OTHER PROCESS PLANTS

(75) Inventors: Subramanian Bhaskaran, Singapore (SG); Angadu Krishnamoorthy (A. K.) Sekar, Singapore (SG)

(73) Assignee: Celanese International Corporation, Dallas, TX (US)

(*) Notice: Subject to any disclaimer, the term of this patent is extended or adjusted under 35 U.S.C. 154(b) by 591 days.

(21) Appl. No.: 10/802,506

(22) Filed: Mar. 17, 2004

(65) Prior Publication Data

US 2005/0209483 A1    Sep. 22, 2005

(51) Int. Cl.
*C07C 67/48* (2006.01)
*C07C 51/10* (2006.01)

(52) U.S. Cl. .................. 560/248; 562/517

(58) Field of Classification Search .......... 562/523, 562/542, 544, 548, 549, 607, 608; 560/231, 560/232

See application file for complete search history.

(56) References Cited

U.S. PATENT DOCUMENTS

| | | | |
|---|---|---|---|
| 3,190,912 A | 6/1965 | Robinson | |
| 3,637,819 A | 1/1972 | Sennewald et al. | |
| 3,650,896 A | 3/1972 | Goeddel | |
| 3,769,329 A | 10/1973 | Paulik et al. | |
| 3,792,087 A | 2/1974 | McClulu et al. | |
| 3,946,068 A | 3/1976 | Calcagno et al. | |
| 3,970,697 A | 7/1976 | Scheben et al. | |
| 4,188,490 A | 2/1980 | Hinnenkamp et al. | |
| 4,370,492 A | 1/1983 | Wunder et al. | |
| 4,654,801 A | 3/1987 | Stewart et al. | |
| 4,902,823 A | 2/1990 | Wunder et al. | |
| 5,001,259 A | 3/1991 | Smith et al. | |
| 5,026,908 A | 6/1991 | Smith et al. | |
| 5,144,068 A | 9/1992 | Smith et al. | |

(Continued)

FOREIGN PATENT DOCUMENTS

WO    WO 98/05620    2/1998

(Continued)

OTHER PUBLICATIONS

Kirk-Orthmer Encyclopedia of Chemical Technology Copyright © 2002 Article Online Posting Date: Jul. 19, 2002 pp. 115-136.*

(Continued)

*Primary Examiner*—Karl J Puttlitz
(74) *Attorney, Agent, or Firm*—Michael W. Ferrell

(57) ABSTRACT

Integrated processes and systems for producing acetic acid and vinyl acetate are provided. In the processes and systems, a portion of the heat produced during the production of the acetic acid is transferred to the vinyl acetate production and/or purification process and system to facilitate production and/or purification of the vinyl acetate product. The process and systems described herein are useful in conjunction with any of the various known processes for the production of acetic acid and vinyl acetate. The heat of the acetic acid production reaction may be transferred to the vinyl acetate production system by any suitable heat transfer processes and systems. The heat may be provided to the purification section at a variety of locations in the vinyl acetate production and purification systems, depending on the specific configuration of the system to which the processes and systems. The process and systems described herein are useful to provide cost and energy savings in vinyl acetate production processes.

10 Claims, 1 Drawing Sheet

U.S. PATENT DOCUMENTS

| | | |
|---|---|---|
| 5,185,308 A | 2/1993 | Bartley et al. |
| 5,189,203 A | 2/1993 | Hansen et al. |
| 5,300,684 A | 4/1994 | Benkalowycz et al. |
| 5,728,871 A | 3/1998 | Joensen et al. |
| 5,952,523 A | 9/1999 | Papavassiliou et al. |
| 6,013,834 A | 1/2000 | Colling |
| 6,040,474 A | 3/2000 | Jobson et al. |
| 6,107,513 A | 8/2000 | Herzog et al. |
| 6,180,821 B1 | 1/2001 | Jobson et al. |
| 6,303,537 B1 | 10/2001 | Wang et al. |
| 6,342,628 B1 | 1/2002 | Williams et al. |
| 6,420,595 B1 | 7/2002 | Hallinan et al. |
| 6,531,630 B2 | 3/2003 | Vidalin |
| 6,596,781 B1 | 7/2003 | Schinski |
| 6,599,491 B2 | 7/2003 | Vidalin |
| 6,602,476 B2 | 8/2003 | Becker et al. |
| 6,605,739 B1 | 8/2003 | Karim et al. |
| 6,790,983 B1 * | 9/2004 | Zeyss et al. .................. 560/208 |
| 2002/0028965 A1 | 3/2002 | Jobson et al. |

OTHER PUBLICATIONS

Wansborough, MUTECH Chemical Enginering Journal (1965), No. 11, 61-7.*

* cited by examiner

UTILIZATION OF ACETIC ACID REACTION HEAT IN OTHER PROCESS PLANTS

FIELD OF THE DISCLOSURE

This disclosure relates to integrated processes and systems for producing acetic acid and vinyl acetate monomers.

BACKGROUND INFORMATION

An important process for the production of acetic acid is the carbonylation of an alkyl alcohol, especially methanol, and reactive derivatives thereof, with carbon monoxide in a liquid reaction medium. Such carbonylation reactions are generally carried out in the presence of a catalyst, e.g., a Group VIII metal catalyst such as rhodium and iridium, a halogen containing catalyst promoter, e.g., methyl iodide, and water. U.S. Pat. No. 3,769,329 discloses the use of a rhodium-based carbonylation catalyst dissolved, or otherwise dispersed, in a liquid reaction medium or supported on an inert solid, along with a halogen-containing catalyst promoter as exemplified by methyl iodide. However, it is understood that various catalyst systems, particularly those incorporating Group VIII metals, may be used for the production of acetic acid through the carbonylation of methanol. Generally, the carbonylation reaction is conducted with the catalyst being dissolved in a liquid reaction medium through which carbon monoxide gas is continuously bubbled. U.S. Pat. No. 3,769,329 discloses that water may be added to the reaction mixture to exert a beneficial effect upon the reaction rate, and water concentrations between about 14 wt. % to about 15 wt. % are typically used. This is sometimes referred to as the "high water" carbonylation process.

An alternative to the "high water" carbonylation process is the "low water" carbonylation process, as described in U.S. Pat. No. 5,001,259, U.S. Pat. No. 5,026,908, and U.S. Pat. No. 5,144,068. Water concentrations below 14 wt. % can be used in the "low water" carbonylation process. Employing a low water concentration simplifies downstream processing of the desired carboxylic acid to its glacial form. The more water there is in a reaction stream, the greater the operating costs to remove water from the product acetic acid and the greater the capital investment in product recovery and purification equipment. The efficiencies achieved when operating at very low water concentrations makes it attractive to operate at the lowest water concentration possible. However, when reducing the reactor water to minimize operating and fixed costs, it is more difficult to maintain acceptably high rates of acetic acid production with good catalyst stability since the rate of the reaction decreases as the reactor water is decreased as explained in U.S. Pat. No. 5,026,908.

Other methods of producing acetic acid include the catalytic oxidation of ethylene. Numerous methods are known for the catalytic oxidation of ethylene to acetic acid. See, for example, U.S. Pat. Nos. 6,605,739; 3,792,087 and 3,970,697.

Vinyl acetate is a well-known industrial chemical. The production of vinyl acetate from ethylene, oxygen and acetic acid using conventional vinyl acetate catalysts is known in the art. Vinyl acetate is typically used as a raw material for vinyl resins such as polyvinyl acetate. Historically, vinyl acetate was primarily manufactured from the vapor phase reaction of ethylene, acetic acid and oxygen with a zinc acetate catalyst. More recently, vinyl acetate is often produced from the vapor-phase reaction of ethylene, acetic acid and oxygen, with palladium-based catalyst systems. For example, it is known to produce vinyl acetate by reaction of ethylene, oxygen and acetic acid using a catalyst comprising palladium and gold, supported on a carrier as described in U.S. Pat. No. 6,303,537. For other exemplary processes, see U.S. Pat. Nos. 3,190,912; 3,637,819; 3,650,896; 4,370,492; 4,902,823, and 5,185,308.

Conventionally, acetic acid and vinyl acetate are produced independently of each other. In other words, vinyl acetate is frequently produced from ethylene wherein a first process involves reacting the ethylene to form acetic acid, followed by a second process of reacting a mixture of the acetic acid and ethylene to produce vinyl acetate.

However, some processes are known to integrate production of the two products in various degrees. For example. U.S. Pat. No. 6,180,821 describes the production of acetic acid and/or vinyl acetate from ethylene, or ethane, using a first reaction zone with a catalyst active for the oxidation of ethylene to acetic acid and/or active for the oxidation of ethane to acetic acid, ethylene and carbon monoxide, and a second reaction zone containing a catalyst active for the production of vinyl acetate. The Patent indicates that an advantage of the integrated process is the heat of the first reaction zone product reduces the need to heat the feed to the second reaction zone. U.S. Pat. No. 4,188,490 relates to a catalytic oxidation process for the production of mixtures of acetic acid and vinyl acetate comprising the step of contacting a feed mixture containing ethylene, oxygen and water, as steam, with a catalyst composition to provide a mixture of acetic acid and vinyl acetate. The catalyst system comprises a palladium metal on a zinc oxide support treated in the presence of a sulfur modifier. The method requires the subsequent step of fractional distillation to separate the acetic acid from the vinyl acetate.

U.S. Pat. Nos. 6,420,595 and 6,605,739 disclose additional integrated processes for the production of acetic acid and vinyl acetate.

BRIEF DESCRIPTION OF THE DISCLOSURE

This disclosure relates to integrated processes and systems for producing acetic acid and vinyl acetate wherein a portion of the heat produced during the production of acetic acid is provided or transferred to the vinyl acetate production and/or purification process and system to facilitate production and/or purification of the vinyl acetate product. The process and systems described herein are useful in conjunction with any of the various known processes for the production of acetic acid and vinyl acetate. For example, the processes and systems described herein are useful in processes and systems in which the acetic acid is produced through carbonylation reactions or through the catalytic oxidation of ethylene and/or ethane. Further, the processes and systems described herein are useful in processes and systems in which vinyl acetate is produced by reacting acetic acid and ethylene in the presence of any type of active catalyst.

Heat generated during acetic acid production may be transferred to vinyl acetate production and/or purification systems by any suitable heat transfer system. The heat may be provided to the production and/or purification systems at a variety of locations, depending on the specific configuration of the systems to which the processes and systems described herein are applied. Exemplary arrangements include transferring the heat of reaction to the acetic acid feed to pre-heat the feed prior to esterification. Alternatively, the heat may be transferred to various components in the vinyl acetate purification section such as a vinyl acetate azeotrope column feed, and reboil streams for vinyl acetate light ends and finishing columns. Alternatively, the processes and systems described herein may be used to allocate portions of the heat transferred among more than one of the locations within the vinyl acetate production process.

The process and systems described herein are useful to provide cost and energy savings in vinyl acetate production processes.

DETAILED DESCRIPTION

Figure 1:
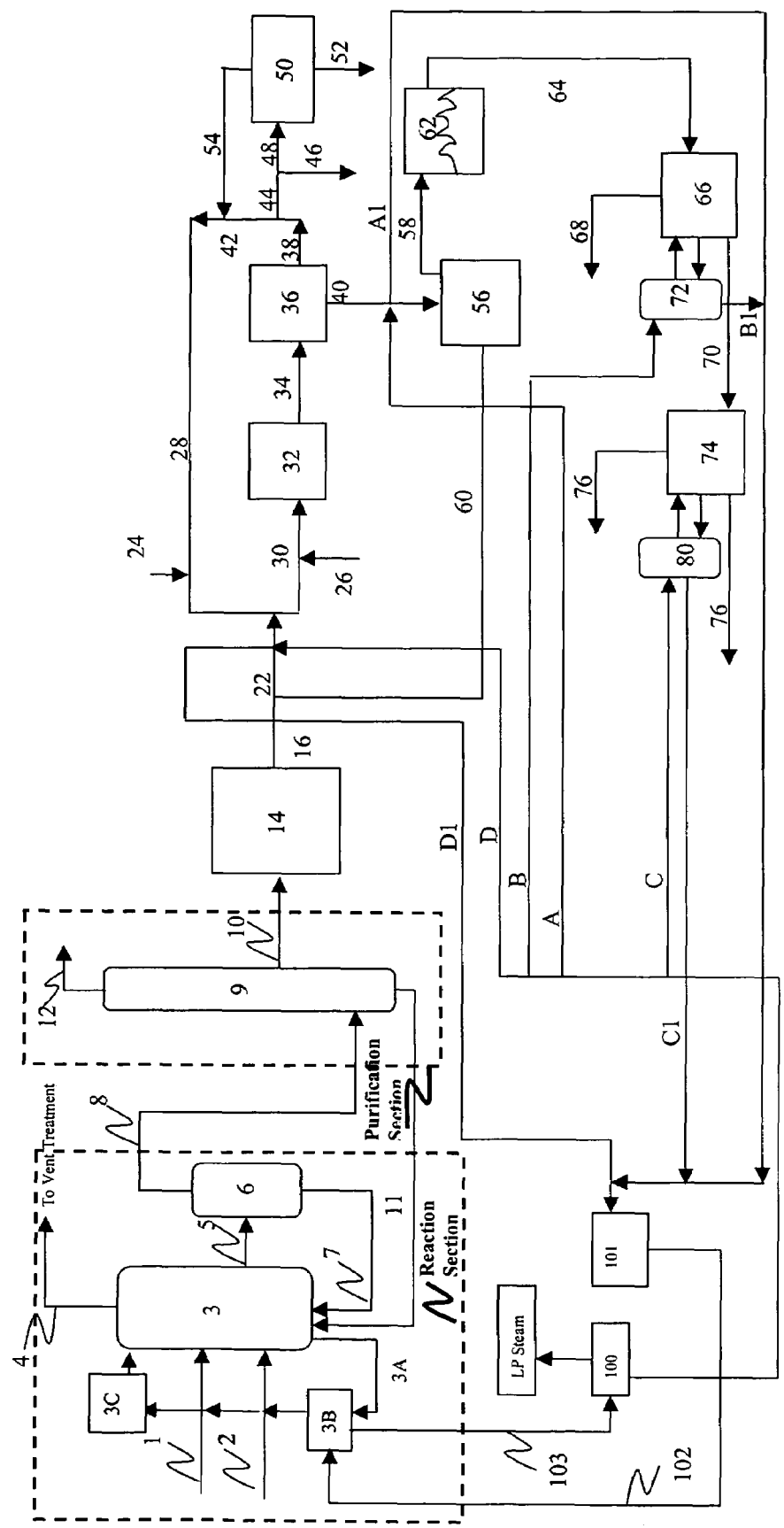
FIG. 1 is a schematic diagram depicting exemplary embodiments of the processes and systems described herein.

The process and systems described herein provide integrated systems for the production of acetic acid and vinyl acetate. More specifically, the processes and systems integrate the use of heat energy liberated during the production of acetic acid between the acetic acid production process and the vinyl acetate production and purification processes. The processes and systems are capable of delivering substantial energy and cost savings in vinyl acetate production and purification processes by productively utilizing heat energy wasted in conventional processes and systems.

The production of acetic acid by way of carbonylation reactions or through the catalytic oxidation of ethylene and/or ethane is an exothermic process. Conventionally, a significant portion of the heat of reaction generated in the production of acetic acid is dissipated, thereby losing the energy produced.

FIG. 1 is a schematic representation of exemplary embodiments of the integrated processes and systems described herein. In the systems depicted, acetic acid is produced by way of a carbonylation reaction, although it is understood that the acetic acid may be produced through other reaction mechanisms such as the oxidation of ethylene and/or ethane. Referring to FIG. 1, continuous streams of an alkyl alcohol and/or reactive derivatives thereof and carbon monoxide are fed through lines 1 and 2 respectively into a stirred reactor 3, or other suitable reactor, containing a reaction liquid comprising an acetic acid solution of a rhodium-based catalyst system, a halogen promoter, a copromoter/stabilizer, water, unreacted akyl alcohol and/or reactive derivatives thereof and carbon monoxide, and impurities such as acetaldehyde and other PRC's, and higher alkyl iodides. The reactor 3 is maintained at conventional temperatures and pressures used in the production of acetic acid. Gases formed in the reactor 3 are withdrawn through line 4 and are sent to vent recovery for the separation of components suitable for recycle to the reactor. Reaction liquid is continuously withdrawn from reactor 3 through line 5 and is fed to flasher 6 where a reduction of pressure causes a portion of the acetic acid and most of the lower boiling compounds to be flashed off as vapor leaving a condensate of the heavier components of the catalyst system.

The flashing process provides partial cooling for the reaction and separates crude acetic acid product from the catalyst. In the embodiment depicted, the cooled flasher condensate is directed through recycle line 7 to reactor 3 while the vapors from flasher 6 are fed through line 8 to light ends or "splitter" column 9 where most of the lower boiling components including methyl iodide, methyl acetate, and acetaldehyde, and a portion of the water are removed overhead. Column 9 is maintained at conventional temperatures and pressures known for the purification of acetic acid. The condensate from flasher 6 may be cooled by conventional means such as a cooling water heat exchanger. Alternatively, the condensate in flasher 6 may be flashed to a second flasher (not shown) where the condensate is cooled through conventional processes such as cooling in fin-fan condensers before recycle to reactor 3. The second flasher may be maintained at conventional temperatures and pressures.

During normal operation, the exothermic reaction taking place in reactor 3 generates more heat than dissipated in the flashing and other process steps described above. Conventionally, this excess heat is dissipated in process steps such as withdrawing a stream directly from the reactor and routing the stream through a series of heat exchangers to remove excess heat. After passing through the heat exchangers, the cooled stream is returned to the reactor. The stream removed from the reactor stream is sometimes referred to as a reactor pump-around stream. These conventional processes result in wasting of the heat energy removed from the pump-around stream.

The processes and systems described herein provide means for productively utilizing the excess heat energy liberated during production of acetic acid. With reference to FIG. 1, in one embodiment in accordance with the processes and systems described herein, a pump-around steam condensate loop is used to absorb at least a portion of the heat of reaction generated in reactor 3 and to productively utilize this heat energy in conjunction with a system for the production and purification vinyl acetate. The details of an exemplary pump-around condensate loop in accordance with this disclosure will be described hereinafter. However, in order to put the use of the pump-around condensate loop in clearer context, the remainder of an exemplary acetic acid purification system and an exemplary vinyl acetate production and purification system will first be described with reference to FIG. 1.

A crude aqueous acetic acid liquid is withdrawn from light ends column 9 through line 10 and sent to the acetic acid recovery system 14, the details of which are not shown. A bottoms fraction comprising some acetic acid and higher boiling components is withdrawn from light ends column 9 through line 11 and recycled to the reaction section. The overhead vapor stream from the light ends column is condensed and fed through line 12 for further processing in accordance with a variety of known additional processing steps, and then a portion of this stream containing methyl iodide, methyl acetate, and some acetic acid is recycled to the reactor or purification section.

Recovered acetic acid 16 is then directed to a vinyl acetate production unit including a reactor 32. The acetic acid steam 16 combines with acetic acid recycle stream 20 forming an acetic acid stream 22. An ethylene stream 24, an oxygen-containing stream, such as an argon-containing oxygen stream, 26 and acetic acid stream 22 are added to ethylene recycle stream 28 forming an ethylene/acetic acid/oxygen stream 30, which is fed into reactor 32. The reactor 32 is maintained at conventional temperatures and pressures used in the production of vinyl acetate. Emerging from reactor 32 is stream 34 that is passed to a scrubbing unit 36. Emerging from the scrubbing unit 36 are two streams, an ethylene-rich stream 38, and a stream 40 containing vinyl acetate and acetic acid. The ethylene-rich stream 38 is separated into streams 42 and 44. Stream 44 is further divided into a purge stream 46, and stream 48 that may be directed to a carbon dioxide removal unit 50. Purge stream 46 is removed. Purified carbon dioxide stream 52 and carbon dioxide-free ethylene effluent stream 54 emerge from carbon dioxide removing unit 50. Purified carbon dioxide stream 52 is removed. Carbon dioxide free ethylene rich effluent stream 54 is added to stream 42 forming recycle stream 28.

The vinyl acetate monomer and acetic acid stream 40 is directed to a purification unit. Within the purification unit, stream 40 is fed to an azeotrope distillation column 56 where vinyl acetate and water is removed as an azeotrope overhead stream 58 and acetic acid and heavy organic by-products are removed as a bottom stream 60 from column 56. The column 56 may be maintained at conventional temperatures and pressures. The water in the overhead stream 58 is separated from vinyl acetate from the vinyl acetate in overhead stream 58 in a decanter 62 and a vinyl acetate product stream 64 is removed from decanter 62. The vinyl acetate product stream 64 is then directed to a light ends column 66 for further purification of the vinyl acetate product. The column 66 may be maintained at conventional temperatures and pressures. The light ends are removed in from the overhead of the light ends column in stream 68 and the vinyl acetate product is removed from the base of the light ends column 66 as stream 70. In the embodiment depicted, a reboiler 72 is provided in conjunction with light ends column 66. The reboiler 72 may be maintained at conventional temperatures and pressures.

In a final purification step, the vinyl acetate product stream 70 is directed to a finishing column 74 for removal of additional light ends in stream 76 and production of a purified vinyl acetate product stream 78. In the embodiment depicted, a reboiler 80 is provided in conjunction with finishing column 74. The reboiler 80 may be maintained at conventional temperatures and pressures.

As mentioned above, an exemplary pump-around condensate loop provided for the purpose of removing and productively using a portion of the heat of reaction from the production of acetic acid is depicted in FIG. 1. The reactor pump-around condensate loop may be used to handle the bulk of the heat of the reaction by the flow of a hot reactor solution stream 3A first through heat exchanger 3B to transfer heat to a steam condensate stream 103. The steam condensate stream 103 is directed to a low pressure flash vessel 100. In one embodiment, the low pressure flash vessel 100 is maintained at a temperature of about 150° C. to about 160° C. and a pressure of about 4.0 kg/cm$^2$ to about 5.3 kg/cm$^2$. The low pressure flash vessel 100 may be used to generate steam as needed at other process locations. Generally, only a small percentage of the heat of reaction is used to produce steam in this manner. For example, in one embodiment, only about 5% of the heat of the reaction is used to produce steam in flash vessel 100.

In accordance with one embodiment of the processes and systems described herein the heat generated in the production of the acetic acid residing in the condensate stream of low pressure flash vessel 100 may be transferred to various locations within the vinyl acetate production and purification and production systems to facilitate production and purification processes. Certain exemplary embodiments of the processes and systems described herein are schematically illustrated in FIG. 1.

In one embodiment, at least a portion of the heat of the acetic acid production reaction is transferred to the feed of the azeotrope column within the purification section for purifying vinyl acetate. In one variation of this embodiment, the heat is transferred from the steam condensate from low pressure flash vessel 100 as depicted in FIG. 1. The heat is transferred from the condensate as depicted by line A to the vinyl acetate azeotrope column feed 40. As noted above, the heat may be removed from the condensate by any means such as a shell and tube heat exchanger or other standard TEMA designs or any other heat exchange equipment. After supplying heat to the azeotrope column feed 40, the condensate is returned to atmospheric flash vessel 101 as stream A1.

Alternatively, heat may be transferred from the hot steam condensate in low pressure steam flash vessel 100 to the reboil 72 of the light ends column 66. Again, the heat may be removed from the condensate by any means such as a shell and tube heat exchanger or other heat exchange equipment and transferred to the reboil 72 as depicted by line B in FIG. 1. The condensate after supplying heat in 72 is returned to atmospheric flash vessel 101 as stream B1.

In another embodiment, the heat may be transferred by any suitable means such as heat exchange equipment from hot steam condensate from the low pressure steam flash vessel 100 to the reboil 80 used in conjunction with finishing column 74 as depicted by line C in FIG. 1. After supplying heat to the reboil 80, the condensate is returned to atmospheric flash vessel 101 as stream C1.

In still another embodiment, the heat may be transferred from the condensate in flash vessel 100 by any suitable means such as heat exchange equipment to preheat the acetic acid feed 22 as depicted by line D in FIG. 1. After supplying heat to the acetic acid feed, the condensate is returned to atmospheric flash vessel 101 as stream D1.

Additionally, as mentioned above, the heat of reaction from the acetic acid production may be transferred simultaneously to more than one location within the vinyl acetate production and purification systems. For example, in one embodiment, at least a portion of the heat of the acetic acid production reaction may be transferred and allocated between the reboil 72 of the light ends column 66 and the reboil 80 of the finishing column 74. In another the at least a portion of the heat of reaction may be transferred and allocated between the reboil 80 of the finishing column 74 and the acetic acid feed 22.

In one embodiment, atmospheric flash vessel 101 is maintained at a temperature of about 110° C. to about 125° C. and a pressure of about 0.5 kg/cm$^2$ to about 2.0 kg/cm$^2$. This lower temperature in vessel 101 enables return of the condensate streams depicted by A1-D1 to be cooled and directed to heat exchanger 3B via stream 102 at a lower temperature. The lower temperature allows for a smaller heat exchanger 3B thereby reducing capital costs by significant amounts especially if heat exchanger 3B if made of zirconium.

Atmospheric flash vessel 101 may also be useful for receiving and cooling the condensate directly from flash vessel 100 under certain circumstances. For example if the vinyl acetate production unit is not operating, flash vessel 101 may be used to provide additional cooling of the condensate from flash vessel 100 before directing the condensate to heat exchanger 3B.

Of course, it is understood that atmospheric flash vessel 101 may be eliminated from certain embodiments in accordance with the processes and systems described herein. Elimination of atmospheric flash vessel 101 would require more cooling capacity in heat exchangers 3A and 3B.

It is understood that the system components in the processes and systems depicted in FIG. 1 and otherwise describer herein are exemplary only and that additional, fewer, and/or different system components may be incorporated in accordance with the processes and systems described herein. It is also understood that the processes and systems described herein may be used to integrate systems for the production of chemicals other than acetic acid and vinyl acetate.

The processes and systems described herein are useful to provide significant energy and cost savings over conventional processes and systems for producing acetic acid and vinyl acetate. The processes and systems described herein are useful for providing energy savings of at least 285 Kcal per kg of vinyl acetate produced.

All patents and publications referred to herein are hereby incorporated by reference in their entireties.

Although the present invention and its advantages have been described in detail, it should be understood that various changes, substitutions, and alterations could be made without departing from the spirit and scope of the invention as defined by the following claims.

What is claimed is:

1. An integrated process for the production of acetic acid and vinyl acetate comprising the steps:
   (a) producing in a first reaction zone a first product stream comprising acetic acid wherein the acetic acid is produced using an exothermic carbonylation reaction, and wherein at least a portion of the heat from the production of acetic acid is removed from the first reaction zone and at least a portion of the heat removed from the production of acetic acid is transferred in a heat transfer system;
   (b) contacting in a second reaction zone an acetic acid reaction stream comprised of at least a portion of the acetic acid from the first product stream with an oxygen-containing gas in the presence of a catalyst to produce a second product stream comprising vinyl acetate monomer;
   (c) directing at least a portion of the second product stream to a purification section for purifying vinyl acetate to purify at least a portion of the vinyl acetate in the second product stream; and
   (d) removing at least a portion of the heat transferred to the heat transfer system and providing at least a portion of the heat removed from the heat transfer system to at least one of the acetic acid reaction stream and the purification section for purifying vinyl acetate, and wherein the heat transfer system comprises a steam condensate stream, and wherein at least a portion of the heat removed from the production of acetic acid is transferred to the steam condensate stream which is used to provide heat removed from the production of acetic acid to at least one of the acetic acid reaction stream and the purification section for purifying vinyl acetate, wherein the stream condensate stream comprising the heat from the production of the acetic acid is transferred into a low pressure flash vessel maintained at a pressure of about 4.0 kg/cm² to about 5.3 kg/cm².

2. The process of claim 1 wherein the flash vessel is maintained at a temperature of about 150° C. to about 160° C.

3. The process of claim 1 wherein heat removed from the production of acetic acid is transferred from the steam condensate of the heat transfer system to a vinyl acetate azeotrope column feed stream.

4. The process of claim 1 wherein the heat removed from the production of acetic acid is transferred from the steam condensate of the heat transfer system to a reboil stream of light ends column in the purification section for purifying vinyl acetate.

5. The process of claim 1 wherein the heat removed from the production of acetic acid is transferred from the steam condensate of the heat transfer system to a reboil stream used in conjunction with a finishing column in the purification section for purifying vinyl acetate.

6. The process of claim 1 wherein the heat removed from the production of acetic acid is transferred from the steam condensate of the heat transfer system to the acetic acid reaction stream.

7. The process of claim 1 wherein the heat removed from the production of acetic acid is transferred from the steam condensate of the heat transfer system to a reboil stream of a light ends column in the purification section for purifying vinyl acetate and to reboil stream used in conjunction with a finishing column in the purification section for purifying vinyl acetate.

8. An integrated process for the production of acetic acid and vinyl acetate comprising the steps:
   (a) producing in a first reaction zone a first product stream comprising acetic acid, wherein the acetic acid is produced using an exothermic carbonylation reaction, and wherein at least a portion of the heat from the production of acetic acid is removed from the first reaction zone and at least a portion of the heat removed from the production of acetic acid is transferred into a heat transfer system;
   (b) contacting in a second reaction zone an acetic acid reaction stream comprised of at least a portion of the acetic acid from the first product stream with an oxygen-containing gas in the presence of a catalyst to produce a second product stream comprising vinyl acetate monomer;
   (c) directing at least a portion of the second product stream to a purification section for purifying vinyl acetate to purify at least a portion of the vinyl acetate in the second product stream; and
   (d) removing at least a portion of the heat transferred to the heat transfer system and providing at least a portion of the heat removed from the heat transfer system to at least one of the acetic acid reaction stream and the purification section for purifying vinyl acetate, wherein the beat transfer system comprises a pump-around condensate loop in which the heat from the production of the acetic acid is removed from the first reaction zone through heat exchange between a hot reactor solution stream and a steam condensate stream, wherein the stream condensate stream comprising the heat from the production of the acetic acid is transferred into a low pressure flash vessel maintained at a pressure of about 4.0 kg/cm² to about 5.3 kg/cm² .

9. The integrated process of claim 8, wherein the flash vessel maintained at a temperature of about 150° C. to about 160° C.

10. The integrated process of claim 8, wherein the heat removed from the production of acetic acid is transferred from the steam condensate of the heat transfer system to the acetic acid reaction stream.

* * * * *